(12) United States Patent
Polzin et al.

(10) Patent No.: US 11,367,179 B2
(45) Date of Patent: Jun. 21, 2022

(54) DETERMINING DEGREE OF MOTION USING MACHINE LEARNING TO IMPROVE MEDICAL IMAGE QUALITY

(71) Applicants: GE Precision Healthcare LLC, Milwaukee, WI (US); Partners Healthcare System, Inc., Boston, MA (US); The General Hospital Corporation, Boston, MA (US); The Brigham and Women's Hospital, Inc., Boston, MA (US)

(72) Inventors: Jason Polzin, Lake Mills, WI (US); Bernardo Bizzo, Boston, MA (US); Bradley Wright, Boston, MA (US); John Kirsch, Boston, MA (US); Pamela Schaefer, Boston, MA (US)

(73) Assignees: GE Precision Healthcare LLC, Milwaukee, WI (US); Partners Healthcare System, Inc., Boston, MA (US); The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 149 days.

(21) Appl. No.: 16/588,129

(22) Filed: Sep. 30, 2019

(65) Prior Publication Data
US 2021/0097679 A1    Apr. 1, 2021

(51) Int. Cl.
*G06T 7/00*   (2017.01)
*A61B 6/03*   (2006.01)
(Continued)

(52) U.S. Cl.
CPC ............ *G06T 7/0012* (2013.01); *A61B 6/032* (2013.01); *A61B 6/505* (2013.01); *G06N 3/08* (2013.01);
(Continued)

(58) Field of Classification Search
CPC . G06N 3/04; G06N 3/08; G06N 20/10; G06T 7/0012; G06T 7/11; G06T 7/136;
(Continued)

(56) References Cited

U.S. PATENT DOCUMENTS

| | | | | |
|---|---|---|---|---|
| 9,672,615 B2* | 6/2017 | Fonte | ..................... | A61B 6/504 |
| 10,729,502 B1* | 8/2020 | Wolf | ..................... | G16H 20/40 |
| 2009/0279672 A1* | 11/2009 | Reiner | ................... | A61B 6/581 |
| | | | | 378/207 |
| 2014/0358585 A1* | 12/2014 | Reiner | ................... | G16H 80/00 |
| | | | | 705/3 |

(Continued)

OTHER PUBLICATIONS

U.S. Appl. No. 16/394,774, filed Apr. 25, 2019.
(Continued)

*Primary Examiner* — Katrina R Fujita
(74) *Attorney, Agent, or Firm* — Amin, Turocy & Watson, LLP

(57) ABSTRACT

Systems and techniques for determining degree of motion using machine learning to improve medical image quality are presented. In one example, a system generates, based on a convolutional neural network, motion probability data indicative of a probability distribution of a degree of motion for medical imaging data generated by a medical imaging device. The system also determines motion score data for the medical imaging data based on the motion probability data.

20 Claims, 11 Drawing Sheets

(51) Int. Cl.
*G06N 3/08* (2006.01)
*G06T 7/11* (2017.01)
*A61B 6/00* (2006.01)
*G06N 20/10* (2019.01)
*G06T 7/136* (2017.01)
*G06N 3/04* (2006.01)

(52) U.S. Cl.
CPC ............... *G06N 20/10* (2019.01); *G06T 7/11* (2017.01); *A61B 6/5205* (2013.01); *G06N 3/04* (2013.01); *G06T 7/136* (2017.01); *G06T 2207/10081* (2013.01); *G06T 2207/30012* (2013.01); *G06T 2210/41* (2013.01)

(58) Field of Classification Search
CPC . G06T 2207/10081; G06T 2207/30012; G06T 2210/41; A61B 6/32; A61B 6/505; A61B 6/5205
See application file for complete search history.

(56) References Cited

U.S. PATENT DOCUMENTS

| | | | |
|---|---|---|---|
| 2016/0000383 A1* | 1/2016 | Lee | A61B 5/24 600/301 |
| 2016/0300370 A1* | 10/2016 | Yoo | G06T 11/006 |
| 2016/0350919 A1* | 12/2016 | Steigauf | G06V 10/451 |
| 2018/0232878 A1* | 8/2018 | Braun | G06T 7/20 |
| 2018/0330059 A1* | 11/2018 | Bates | G16H 50/30 |
| 2020/0160511 A1* | 5/2020 | Lyman | G06F 16/245 |
| 2020/0302619 A1* | 9/2020 | Lu | G06T 11/003 |
| 2021/0012162 A1* | 1/2021 | Huang | G06K 9/6262 |

OTHER PUBLICATIONS

U.S. Appl. No. 16/394,786, filed Apr. 25, 2019.
U.S. Appl. No. 16/394,791, filed Apr. 25, 2019.
Beque et al., "Generic feature extraction accompanied by support vector classification: an efficient and effective way for MR image quality determination", Proceedings 28th ISMRM, Jun. 2018, p. 2859.

* cited by examiner

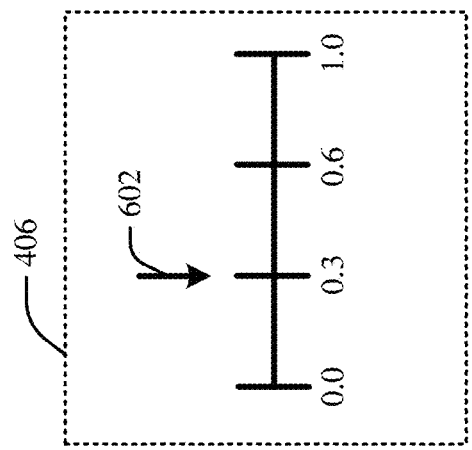
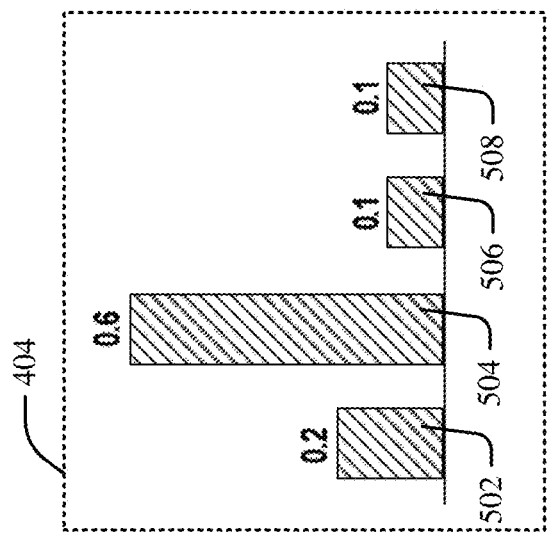
FIG. 6

DETERMINING DEGREE OF MOTION USING MACHINE LEARNING TO IMPROVE MEDICAL IMAGE QUALITY

TECHNICAL FIELD

This disclosure relates generally to machine learning and/or artificial intelligence related to medical imaging.

BACKGROUND

A medical imaging device such as a magnetic resonance imaging (MRI) device is often employed to generate medical images to facilitate detection and/or diagnosis of a medical condition for a patient. For example, an MRI scan can be performed to acquire medical images regarding an anatomical region to facilitate detection and/or diagnosis of a medical condition associated with the anatomical region. However, in certain scenarios, a patient can move during an MRI scan which can introduce a certain amount of motion to a medical image acquired via the MRI scan. An amount of motion introduced to a medical image is generally a subjective measure. Therefore, a human such as a radiologist generally determines whether image quality of a medical image has deteriorated to a point where a rescan is needed. As such, conventional medical imaging techniques can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system comprises a memory that stores computer executable components. The system also comprises a processor that executes the computer executable components stored in the memory. The computer executable components comprise a machine learning component and a scoring component. The machine learning component generates, based on a convolutional neural network, motion probability data indicative of a probability distribution of a degree of motion for medical imaging data generated by a medical imaging device. The scoring component that determines motion score data for the medical imaging data based on the motion probability data.

According to another embodiment, a method is provided. The method provides for employing, by a system comprising a processor, a convolutional neural network to generate motion probability data indicative of a probability distribution of a degree of motion for medical imaging data generated by a medical imaging device. The method also provides for determining, by the system, motion score data for the medical imaging data based on the motion probability data.

According to yet another embodiment, a computer readable storage device comprising instructions that, in response to execution, cause a system comprising a processor to perform operations. The operations comprise generating, using a convolutional neural network, motion probability data indicative of a probability distribution of a degree of motion for medical imaging data generated by a medical imaging device. The operations also comprise determining motion score data for the medical imaging data based on the motion probability data.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which:

FIG. 6 illustrates an example system associated with probability distribution of degree of motion and/or a motion score, in accordance with one or more embodiments described herein;

DETAILED DESCRIPTION

Figure 1:
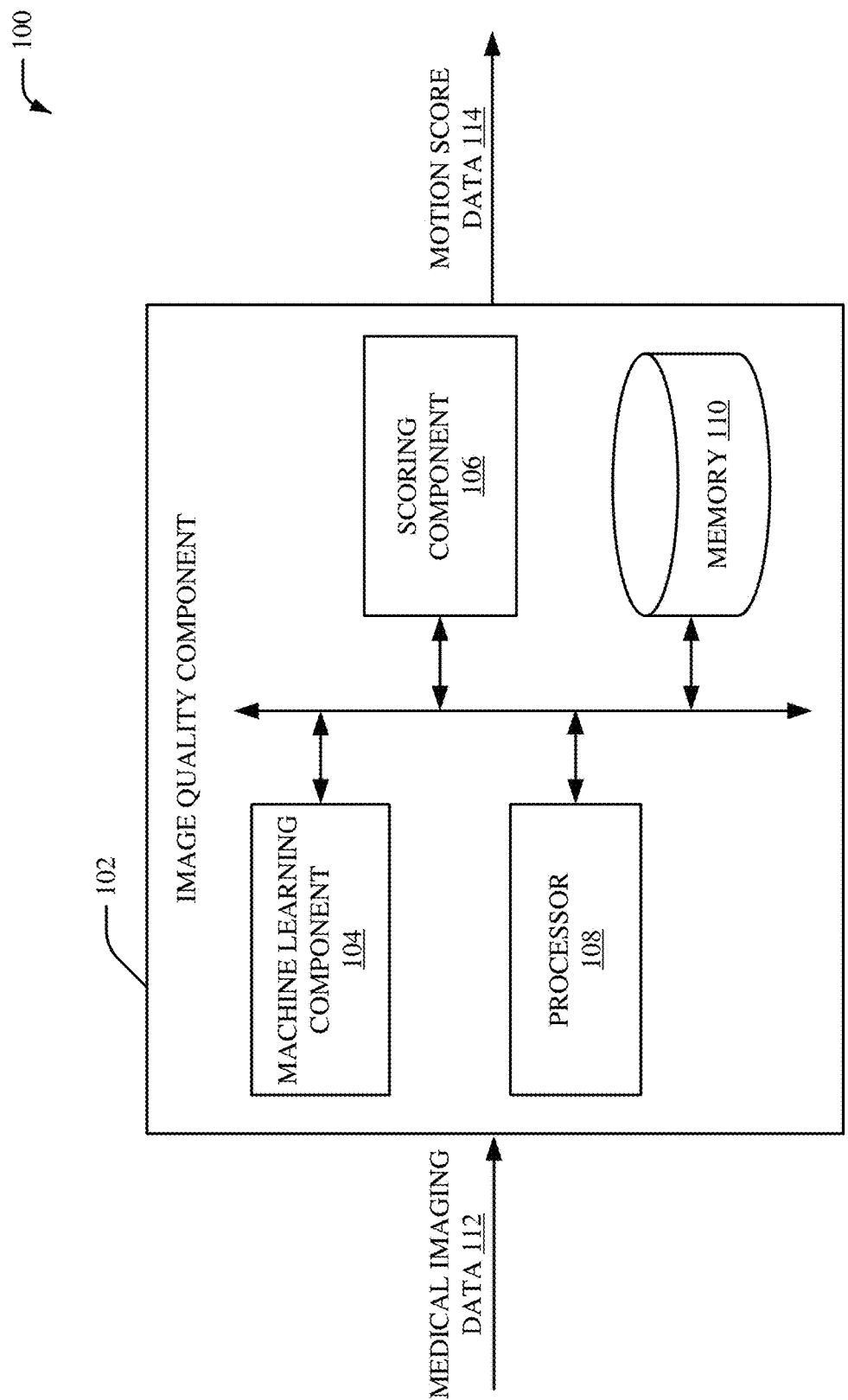
FIG. 1 illustrates a high-level block diagram of an example image quality component, in accordance with one or more embodiments described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for determining degree of motion using machine learning to improve medical image quality are presented. For instance, one or more machine learning techniques can be employed to facilitate identifying presence of image quality issues in medical images generated by a medical imaging device. In an embodiment, a medical image can be captured by a medical imaging device. In an example, a magnetic resonance imaging (MRI) image can be generated by an MRI device during an MRI scan. Furthermore, a machine learning model can be executed to analyze the medical image (e.g., the MRI image) and to determine a motion score for the medical image. A rescan by the medical imaging device (e.g., the MRI device) can be initiated in response to a determination that the motion score satisfies a defined threshold value. In certain embodiments, the machine learning mode can output a probability distribution of a degree of motion in the medical image (e.g., the MRI image). Additionally, the probability distribution can be converted into the motion score. In certain embodiment, the probability distribution can be converted into the motion score by calculating a normalized expected value of the probability distribution. In an aspect, subjective motion information for model training can be quantified. In certain embodiments, model performance can be tested in an environment where a ground truth is highly variable. In certain embodiments, a machine learning model can be provided to analyze a medical image series or sequence of medical images. The machine learning model can also provide a set of outputs that facilitate detection and/or diagnosis of a medical condition. As such, accuracy of medical condition diagnosis can be improved. Furthermore, management of medical image quality issues can be improved. Patient recall for a medical procedure can also be reduced Image quality includes, but is not limited to, presence of imaging artifacts, inadequate anatomic coverage, insufficient contrast, incomplete examination, post-processing error, missing reconstructions, and/or another type of image quality characteristic. As such, by employing systems and/or techniques disclosed herein for determining degree of motion using machine learning, quality of medical imaging data can be improved. Additionally, detection and/or localization of medical conditions for a patient associated with medical imaging data can also be improved. Accuracy and/or efficiency for classification and/or analysis of medical imaging data can also be improved. Moreover, effectiveness of a machine learning model for classification and/or analysis of medical imaging data can be improved, performance of one or more processors that execute a machine learning model for classification and/or analysis of medical imaging data can be improved, and/or efficiency of one or more processors that execute a machine learning model for classification and/or analysis of medical imaging data can be improved.

Referring initially to FIG. 1, there is illustrated an example system 100 that facilitates determining degree of motion using machine learning to improve medical image quality, according to one or more embodiments of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In certain embodiments, the system 100 can be associated with a viewer system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include an image quality component 102 that can include a machine learning component 104 and a scoring component 106. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the image quality component 102) can include memory 110 for storing computer executable components and instructions. The system 100 (e.g., the image quality component 102) can further include a processor 108 to facilitate operation of the instructions (e.g., computer executable components and instructions) by the system 100 (e.g., the image quality component 102).

The image quality component 102 (e.g., the machine learning component 104) can receive medical imaging data 112. The medical imaging data 112 can be two-dimensional medical imaging data and/or three-dimensional medical imaging data generated by one or more medical imaging devices. For instance, the medical imaging data 112 can be electromagnetic radiation imagery captured via a set of sensors (e.g., a set of sensors associated with a medical imaging device). In certain embodiments, the medical imaging data 112 can be a series of electromagnetic radiation imagery captured via a set of sensors (e.g., a set of sensors associated with a medical imaging device) during an interval of time. The medical imaging data 112 can be received directly from one or more medical imaging devices. Alternatively, the medical imaging data 112 can be stored in one or more databases that receives and/or stores the medical imaging data associated with the one or more medical imaging devices. A medical imaging device can be, for example, an MRI device, an x-ray device, a computed tomography (CT) device, another type of medical imaging device, etc. In one example, the medical imaging data 112 can include one or more MRI images. In another example, the medical imaging data 112 can include a T2 axial MRI image, a FLAIR axial MRI image, a T1 sagittal MRI image, a T1 axial pre contrast MRI image, a T1 axial post contrast MRI image, a diffusion-weighted MRI image, a T2-based MRI image, and/or another type of MRI image.

The machine learning component 104 can generate motion probability data based on analysis of the medical imaging data 112. The motion probability data can be indicative of a probability distribution of a degree of motion for the medical imaging data 112. For instance, the motion probability data can be indicative of a probability distribution of a degree of motion introduced during a scan performed via a medical imaging device. In an example, the motion probability data can be indicative of a probability distribution of a degree of motion for an MRI image generated during an MRI scan by an MRI device. The machine learning component 104 can analyze the medical imaging data 112 using one or more machine learning techniques to generate the motion probability data. In an embodiment, the machine learning component 104 can generate the motion probability data based on a convolutional neural network. The convolutional neural network can include a set of convolutional layers associated with upsampling and/or downsampling. Furthermore, in certain embodiments, the convolutional neural network can include a contracting path of convolutional layers and/or an expansive path of convolutional neural layers. In another embodiment, the machine learning component 104 can generate the motion probability data based on an artificial recurrent neural network. The artificial recurrent neural network can include a set of convolutional layers associated with upsampling and/or downsampling. In certain embodiments, the artificial recurrent neural network can include a contracting path of convolutional layers and/or an expansive path of convolutional neural layers. Furthermore, the artificial recurrent neural network can employ context data associated with previous inputs provided to the artificial recurrent neural network and/or previous outputs provided by the artificial recurrent neural network to analyze the medical imaging data 112. In yet another embodiment, the machine learning component 104 can generate the motion probability data based on a convolutional neural network (CNN) Long Short-Term Memory (LSTM) network. The CNN LSTM network can employ one or more convolutional layers for feature extraction associated with the medical imaging data 112. Furthermore, the CNN LSTM network can employ a Long Short-Term Memory network that includes one or more feedback connections, one or more cells, one or more input gates, one or more output gates and/or one or more forget gates for sequence prediction related to the medical imaging data 112.

In certain embodiments, the machine learning component 104 can extract information that is indicative of correlations, inferences and/or expressions from the medical imaging data 112 based on a convolutional neural network associated with a network of convolutional layers. Additionally or alternatively, the machine learning component 104 can generate the motion probability data (e.g., the probability distribution of a degree of motion for the medical imaging data 112) based on the correlations, inferences and/or expressions. The machine learning component 104 can generate the motion probability data based on the execution of at least one machine learning model associated with a network of convolutional layers. In an aspect, the machine learning component 104 can perform learning with respect to the medical imaging data 112 explicitly or implicitly using a network of convolutional layers. The machine learning component 104 can also employ an automatic classification system and/or an automatic classification process to facilitate analysis of the medical imaging data 112. For example, the machine learning component 104 can employ a probabilistic and/or statistical-based analysis (e.g., factoring into the analysis utilities and costs) to learn and/or generate inferences with respect to the medical imaging data 112. The machine learning component 104 can employ, for example, a support vector machine (SVM) classifier to learn and/or generate inferences for medical imaging data 112. Additionally or alternatively, the machine learning component 104 can employ other classification techniques associated with Bayesian networks, decision trees and/or probabilistic classification models. Classifiers employed by the machine learning component 104 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, x=(x1, x2, x3, x4, xn), to a confidence that the input belongs to a class—that is, f(x)=confidence (class).

The scoring component 106 can determine motion score data 114 for the medical imaging data 112 based on the motion probability data determined by the machine learning component 104. The motion score data 114 can include a motion score that defines a degree of motion (e.g., an amount of motion) in the medical imaging data 112. For example, the motion score data 114 can indicate whether the medical imaging data 112 is associated with no motion introduced during a scan process that generates the medical imaging data 112, mild motion introduced during the scan process that generates the medical imaging data 112, moderate motion introduced during the scan process that generates the medical imaging data 112, or severe motion introduced during a scan process that generates the medical imaging data 112. In certain embodiments, the scoring component 106 can determine the motion score data 114 based on context data indicative of context with the medical imaging data 112 with respect to a medical condition. For instance, a value of the motion score data can be modified (e.g., weighted) based on the context data. The context data can include, for example, a degree of criticality for accuracy. For example, a routine scan for a patient that is performed once every year to determine presence or non-presence of a medical condition can comprise a lower degree of criticality for accuracy than a first scan for a potentially life threatening medical condition for a patient. Additionally or alternatively, the scoring component 106 can determine the motion score data 114 based on context data indicative of context with the medical imaging data 112 with respect to a patient identity. For example, a medical history of a patient can determine a degree of criticality for accuracy for a scan. In an embodiment, the scoring component 106 can calculate a normalized expected value of the probability distribution included in the motion probability data to generate the motion score data 114. For example, the scoring component 106 can convert data associated with the probability distribution into a grading scale (e.g., a grading scale with possible values between 0 and 1).

In certain embodiments, the machine learning component 104 can generate first motion probability data for a first portion of the medical imaging data 112. Furthermore, the machine learning component 104 can generate second motion probability data for a second portion of the medical imaging data 112. For example, the machine learning component 104 can generate first motion probability data for a first medical image associated with an anatomical region. The machine learning component 104 can also generate second motion probability data for a second medical image associated with the anatomical region. In certain embodiments, the first medical image can be generated during a first scan process performed by a medical imaging device. Furthermore, the second medical image can be generated during a second scan process performed by the medical imaging device or another medical imaging device. Alternatively, in certain embodiments, the first medical image and the second medical image can be generated during a corresponding scan process associated with a series of medical images (e.g., a sequence of medical images obtained during a scan process). In certain embodiments, the first medical image can be associated with a first scan plane with respect to visualization of an anatomical region and the second medical image can be associated with a second scan plane with respect to visualization of the anatomical region. Additionally or alternatively, in certain embodiments, the first medical image can be associated with a first scan technique with respect to an anatomical region and the second medical image can be associated with a second scan technique with respect to the anatomical region. Additionally or alternatively, in certain embodiments, the first medical image can be associated with a first sequence radio frequency pulses with respect to an anatomical region and the second medical image can be associated with a second sequence of radio frequency pulses with respect to the anatomical region. Additionally or alternatively, in certain embodiments, the first medical image can be associated with a first repetition time between pulse sequence with respect to an anatomical region and the second medical image can be associated with a second repetition time between pulse sequences with respect to the anatomical region. Additionally or alternatively, in certain embodiments, the first medical image can be associated with a first time to echo between pulse sequence with respect to an anatomical region and the second medical image can be associated with a second time to echo between pulse sequences with respect to the anatomical region. In one example, the first medical image can be a T1-weighted image and the second medical image can be a T2-weighted image. In another example, the first medical image can be a FLAIR image and the second medical image can be a T2-weighted image. In yet another example, the first medical image can be a T1-weighted and the second medical image can be a FLAIR image. In certain embodiments, the first medical image and the second medical image can be associated with different contrast levels and/or different brightness levels. Additionally, in an embodiment, the scoring component 106 can determine the motion score data 114 based on a comparison of the first motion probability data and the second motion probability data. For example, the scoring component 106 can perform a series to series comparison of motion to determine a degree of motion in the medical imaging data 112.

In certain embodiments, the scoring component 106 can compare the motion score data 114 to user feedback data regarding a degree of motion in the medical imaging data 112. For example, the scoring component 106 can determine accuracy of the motion score data 114 by comparing the motion score data 114 to user feedback data regarding a degree of motion in the medical imaging data 112. In an embodiment, the scoring component 106 can determine whether the motion score data 114 is within a certain degree of motion as compared to user feedback data regarding a degree of motion in the medical imaging data 112. For instance, in an embodiment, the scoring component 106 can determine that the motion score data 114 is accurate in response to a determination that a degree of motion provided by the user feedback data corresponds to the degree of motion provided in the motion score data 114. In another embodiment, the scoring component 106 can determine that the motion score data 114 is accurate in response to a determination that the user feedback data regarding a degree of motion in the medical imaging data 112 is within one degree of separation as compared to the motion score data 114. For example, the scoring component 106 can determine that the motion score data 114 is accurate in response to a determination that the motion score data 114 indicates mild motion and the user feedback data indicates no motion. In another example, the scoring component 106 can determine accuracy of the motion score data 114 by accessing model performance on continuous scale comparing relative motion between medical images. For instance, the scoring component 106 can determine that the motion score data 114 is accurate in response to a determination that the user feedback data correctly determines, based on the motion score data 114, a ranking of motion for a medical image associated with the medical imaging data 112 as compared to one or more other medical images (e.g., the user feedback data correctly determines which medical image has higher motion). In certain embodiments, the scoring component 106 can determine that the motion score data 114 is accurate based on a comparison between a first ranking of medical images determined by the motion score data 114 and a second ranking of medical images provided by the user feedback data.

In certain embodiments, the motion score data 114 can be employed to facilitate classification and/or localization of one or more medical conditions associated with the medical imaging data 112. For example, the scoring component 106 can employ the motion score data 114 to determine whether image quality of the medical imaging data 112 is satisfactory for a deep learning process associated with classification and/or localization of one or more medical conditions. In certain embodiments, in response to a determination based on the motion score data 114 that image quality of the medical imaging data 112 satisfies a defined criterion (e.g. that image quality of the medical imaging data 112 is satisfactory for a deep learning process associated with medical condition diagnosis), classification and/or localization of a medical condition associated with the medical imaging data 112 can be performed via one or more machine learning techniques. In an embodiment, a classification and/or an associated localization for a portion of an anatomical region associated with the medical imaging data 112 can be determined based on learned medical imaging output associated with a convolutional neural network. In certain embodiments, one or more confidence scores for a classification and/or a localization can be determined. For example, a first portion of the anatomical region with a greatest likelihood of a disease can be assigned a first confidence score, a second portion of the anatomical region with a lesser degree of likelihood of a disease can be assigned a second confidence score, etc. A medical condition classified and/or localized can include, for example, a brain condition, a lung condition, a heart condition, a tissue condition, a bone condition, a tumor, a cancer, tuberculosis, cardiomegaly, hypoinflation of a lung, opacity of a lung, hyperdistension, a spine degenerative condition, calcinosis, or another type of medical condition associated with an anatomical region of a patient body.

It is to be appreciated that technical features of the image quality component 102 (e.g., the machine learning component 104, the scoring component 106 and/or the alert component 202) are highly technical in nature and not abstract ideas. Processing threads of the image quality component 102 (e.g., the machine learning component 104, the scoring component 106 and/or the alert component 202) that process and/or analyze the medical imaging data 112, perform a machine learning process, generate the motion score data 114, etc. cannot be performed by a human (e.g., are greater than the capability of a single human mind). For example, the amount of the medical imaging data 112 processed, the speed of processing of the medical imaging data 112 and/or the data types of the medical imaging data 112 processed by the image quality component 102 (e.g., the machine learning component 104, the scoring component 106 and/or the alert component 202) over a certain period of time can be respectively greater, faster and different than the amount, speed and data type that can be processed by a single human mind over the same period of time. Furthermore, the medical imaging data 112 processed by the image quality component 102 (e.g., the machine learning component 104, the scoring component 106 and/or the alert component 202) can be one or more medical images generated by sensors of a medical imaging device. Moreover, the image quality component 102 (e.g., the machine learning component 104, the scoring component 106 and/or the alert component 202) can be fully operational towards performing one or more other functions (e.g., fully powered on, fully executed, etc.) while also analyzing the medical imaging data 112.

Figure 2:
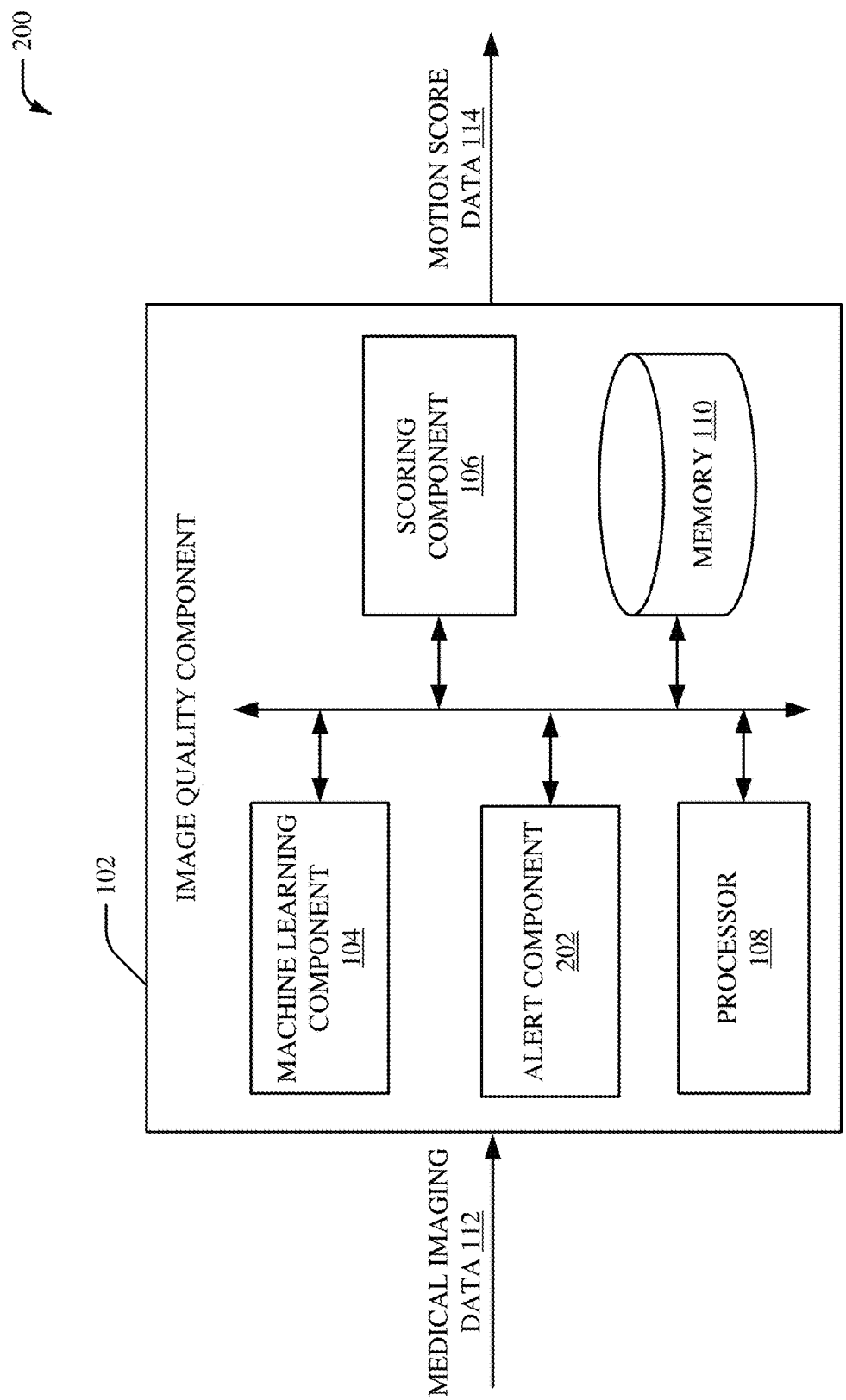
FIG. 2 illustrates a high-level block diagram of another example image quality component, in accordance with one or more embodiments described herein.

FIG. 2 illustrates an example, non-limiting system 200 in accordance with one or more embodiments described herein. Repetitive description of like elements employed in other embodiments described herein is omitted for sake of brevity. The system 200 includes the image quality component 102. In the embodiment shown in FIG. 2, the image quality component 102 can include the machine learning component 104, the scoring component 106, an alert component 202, the processor 108 and/or the memory 110. The alert component 202 can generate and/or transmit one or more alerts based on the motion score data 114. For instance, the alert component 202 can transmit one or more alerts in response to a determination that the motion score data 114 satisfies a defined criterion. An alert generated and/or transmitted by the alert component 202 can be a message and/or a notification to provide machine-to-person communication related to the motion score data 114. Furthermore, an alert generated and/or transmitted by the alert component 202 can include textual data, audio data, video data, graphic data, graphical user interface data, and/or other data. In one example, the alert component 202 can transmit one or more alerts in response to a determination that a value of a motion score included in the motion score data 114 is equal to or above a defined threshold value. In an embodiment, the alert component 202 can transmit one or more alerts via a medical imaging device. For example, the alert component 202 can transmit one or more alerts as an audio message broadcasted by a medical imaging device. In another example, the alert component 202 can transmit one or more alerts in a human-interpretable format for a graphical user interface of a medical imaging device. Additionally or alternatively, in another embodiment, the alert component 202 can transmit one or more alerts via a user device. For example, the alert component 202 can transmit one or more alerts in a human-interpretable format for a graphical user interface of a user device. In another example, the alert component 202 can transmit one or more alerts as an audio message broadcasted by a user device. A user device can be a screen, a monitor, a projector wall, a computing device, an electronic device, a desktop computer, a laptop computer, a smart device, a smart phone, a mobile device, a handheld device, a tablet device, a virtual reality device, a portable computing device, or another display device associated with a display configured to present information associated with the motion score data 114 in a human-interpretable format.

Figure 3:
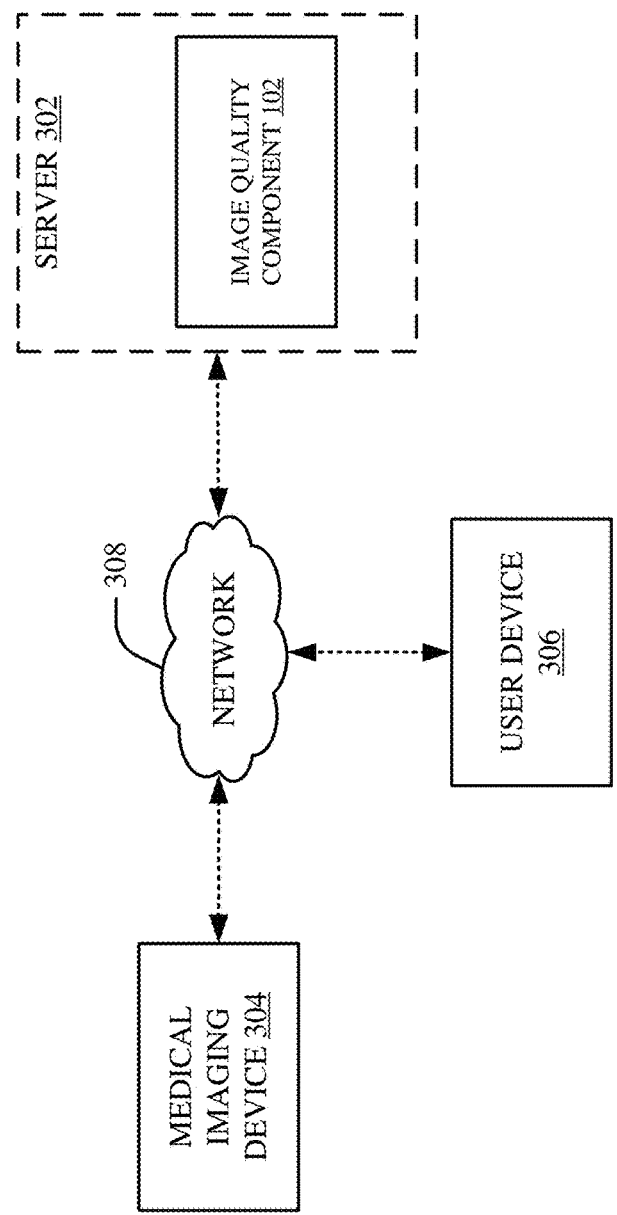
FIG. 3 illustrates an example system that facilitates determining degree of motion using machine learning to improve medical image quality, in accordance with one or more embodiments described herein.

FIG. 3 illustrates an example, non-limiting system 300 in accordance with one or more embodiments described herein. Repetitive description of like elements employed in other embodiments described herein is omitted for sake of brevity.

The system 300 can be, for example, a network environment (e.g., a network computing environment, a healthcare network environment, etc.) to facilitate determining degree of motion using machine learning to improve medical image quality. The system 300 includes a server 302, a medical imaging device 304 and/or a user device 306. The server 302 can include the image quality component 102. The image quality component 102 can include the machine learning component 104, the scoring component 106, the alert component 202, the processor 108 and/or the memory 110. In certain embodiments, the image quality component 102 can be alternatively included in the medical imaging device 304. In certain embodiments, a portion of the image quality component 102 can be included in the server 302 and another portion of the image quality component 102 can be included in the medical imaging device 304. The medical imaging device 304 can generate, capture and/or process at least a portion of the medical imaging data 112. The medical imaging device 304 can be one or more medical imaging devices. For instance, the medical imaging device 304 can include one or more MRI devices, one or more CT devices, one or more PET devices, one or more CAT devices, one or more ultrasound devices, and/or one or more other types of medical imaging devices. In an aspect, the medical imaging device 304 can include a set of sensors to facilitate generating, capturing and/or processing at least a portion of the medical imaging data 112. The user device 306 can be an electronic device associated with a display. For example, the user device 306 can be a screen, a monitor, a projector wall, a computing device, an electronic device, a desktop computer, a laptop computer, a smart device, a smart phone, a mobile device, a handheld device, a tablet device, a virtual reality device, a portable computing device, or another display device associated with a display configured to present information associated with the motion score data 114 in a human-interpretable format. In an embodiment, the user device 306 can include a graphical user interface to facilitate display of information associated with the motion score data 114 in a human-interpretable format. Additionally or alternatively, the user device 306 can include one or more speakers to facilitate broadcast of audio data associated with the motion score data 114. In certain embodiments, the user device 306 can receive one or more alerts from the image quality component 102 (e.g., the alert component 202) of the server 302. Additionally or alternatively, in certain embodiments, the medical imaging device 304 can receive one or more alerts from the image quality component 102 (e.g., the alert component 202) of the server 302. In an embodiment, the server 302 can be in communication with the medical imaging device 304 and/or the user device 306 via a network 308. The network 308 can be a communication network, a wireless network, a wired network, an internet protocol (IP) network, a voice over IP network, an internet telephony network, a mobile telecommunications network or another type of network. In certain embodiments, visual characteristics (e.g., color, size, hues, shading, etc.) of a visual element associated with the motion score data 114 and/or presented via the user device 306 can be altered based on a value of the motion score data 114. In certain embodiments, a user can view, analyze and/or interact with the medical imaging data 112 and/or the motion score data 114 via the user device 306. In an embodiment, the machine learning component 104 can generate the motion probability data and/or the scoring component can generate the motion score data 114 after a scan is performed by the medical imaging device 304 and/or after the medical imaging data 112 is acquired. In another embodiment, the machine learning component 104 can generate the motion probability data and/or the scoring component can generate the motion score data 114 while a scan is being performed by the medical imaging device 304 and/or while an image sequence associated with the medical imaging data 112 is being acquired.

Figure 4:
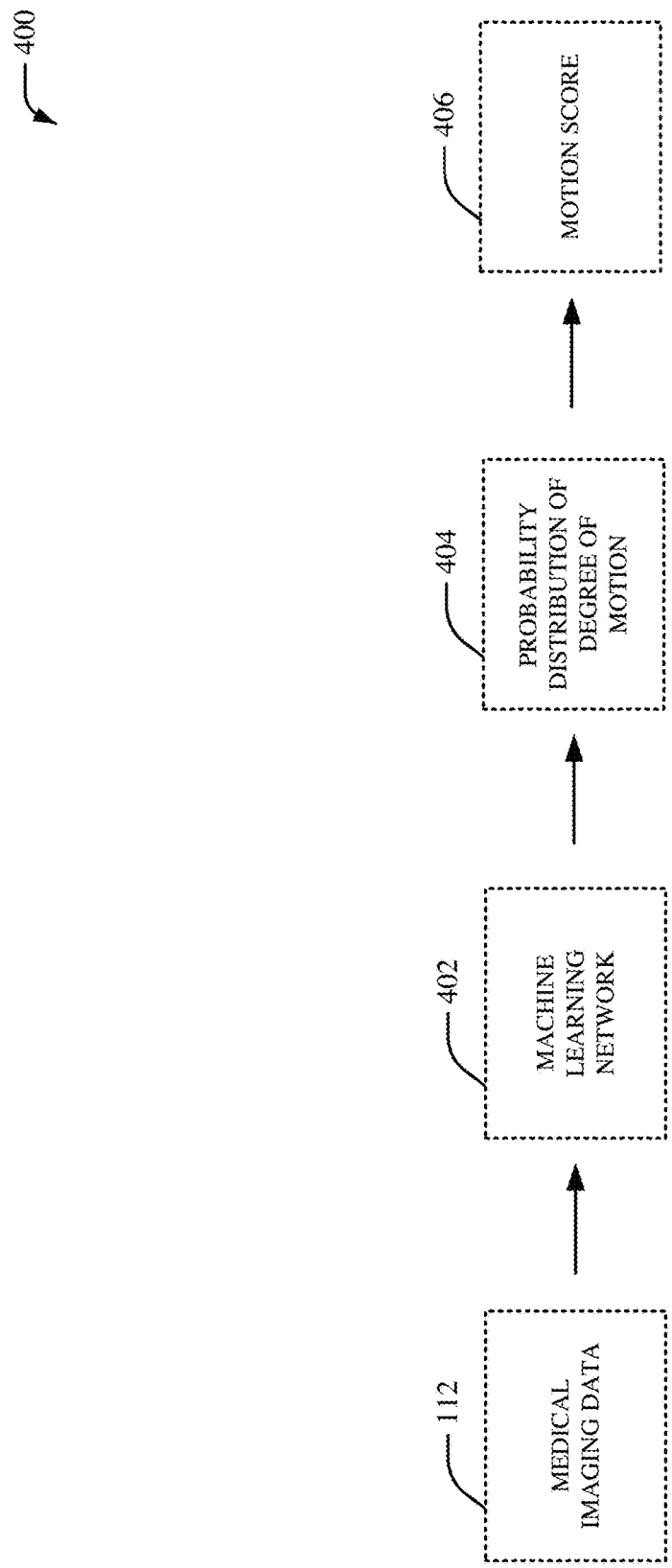
FIG. 4 illustrates another example system that facilitates determining degree of motion using machine learning, in accordance with one or more embodiments described herein.

FIG. 4 illustrates an example, non-limiting system 400 in accordance with one or more embodiments described herein. Repetitive description of like elements employed in other embodiments described herein is omitted for sake of brevity. The system 400 includes a machine learning network 402 that generates a probability distribution of degree of motion 404 based on the medical imaging data 112. The machine learning network 402 can be, for example, a machine learning network 402 employed by the machine learning component 104 to generate the motion probability data. For instance, the motion probability data can include the probability distribution of degree of motion 404. In an embodiment, the machine learning network 402 can be a convolutional neural network. In another embodiment, the machine learning network 402 can be an artificial recurrent neural network. In yet another embodiment, the machine learning network 402 can be a CNN LSTM network. However, it is to be appreciated that the machine learning network 402 can be a different type of machine learning network that generates the probability distribution of degree of motion 404 based on analysis of the medical imaging data 112. Furthermore, a motion score 406 can be generated based on the probability distribution of degree of motion 404. For example, the scoring component 106 can generate the motion score 406 based on the probability distribution of degree of motion 404. The motion score data 114 can include the motion score 406, for example. In certain embodiments, the scoring component 106 can calculate a normalized expected value of the probability distribution of degree of motion 404 to generate the motion score 406.

Figure 5:
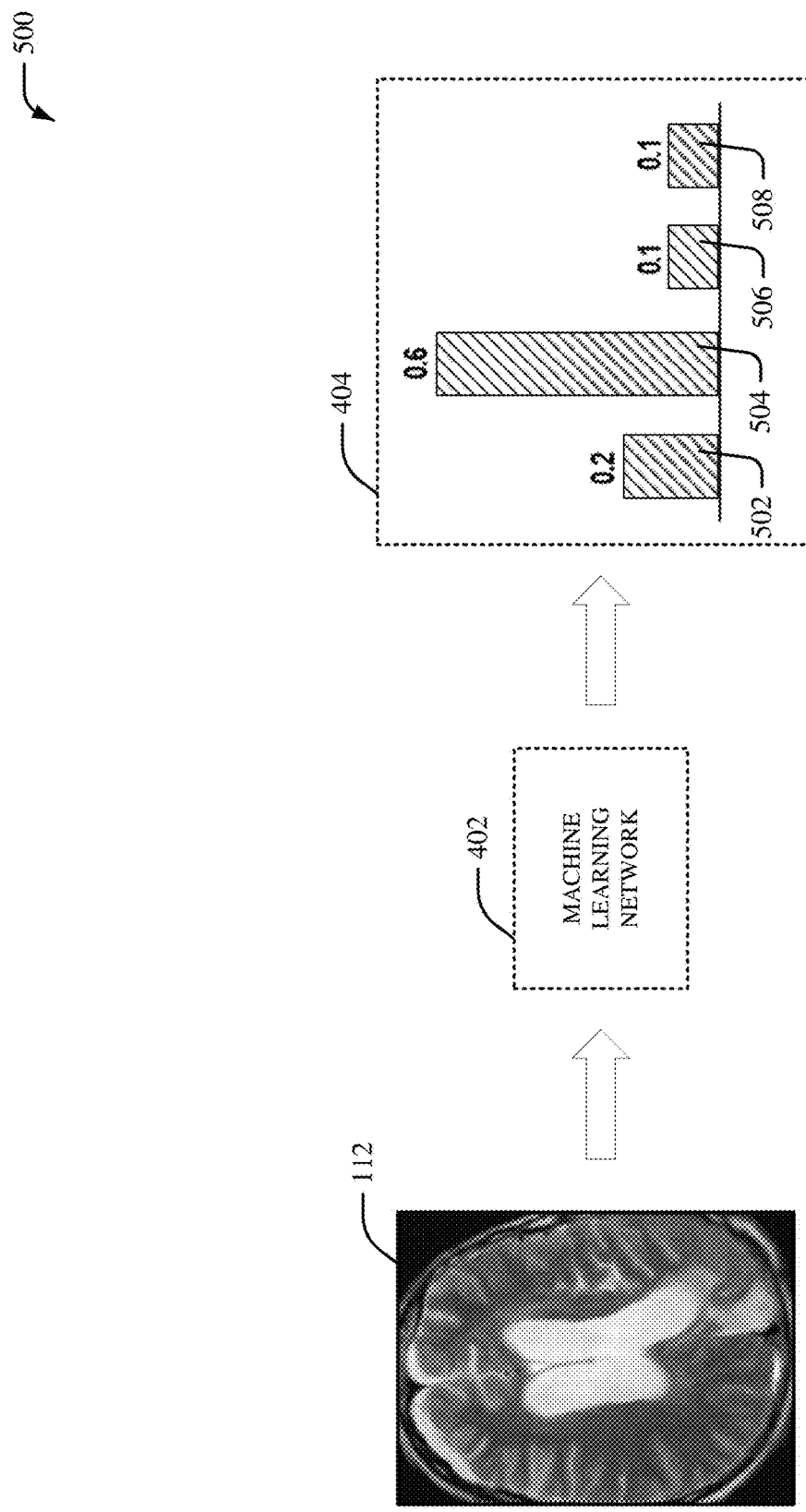
FIG. 5 illustrates an example system associated with a machine learning network, in accordance with one or more embodiments described herein.

FIG. 5 illustrates an example, non-limiting system 500 in accordance with one or more embodiments described herein. Repetitive description of like elements employed in other embodiments described herein is omitted for sake of brevity. The system 500 includes the machine learning network 402 that generates the probability distribution of degree of motion 404 based on the medical imaging data 112. In the embodiment shown in FIG. 5, the probability distribution of degree of motion 404 includes a grading scale with a first classification 502, a second classification 504, a third classification 506 and a fourth classification 508. For example, the first classification 502 can correspond to no motion in the medical imaging data 112, the second classification 504 can correspond to mild motion in the medical imaging data 112, the third classification 506 can correspond to moderate motion in the medical imaging data 112, and the fourth classification 508 can correspond to severe motion in the medical imaging data 112. For example, the second classification 504 that corresponds to mild motion in the medical imaging data 112 can include noticeable motion that generally does not affect reading of the medical imaging data 112 by a medical professional. The third classification 506 that corresponds to moderate motion in the medical imaging data 112 can include noticeable motion that generally affects reading of the medical imaging data 112 by a medical professional while main anatomical structures are visible in the medical imaging data 112. Furthermore, the fourth classification 508 that corresponds to severe motion in the medical imaging data 112 can include very noticeable motion where features of the medical imaging data 112 generally cannot be read by a medical professional and a rescan by a medical imaging device (e.g., by the medical imaging device 304) is generally required. In the non-limiting example shown in FIG. 5, the probability distribution of degree of motion 404 can indicate a probability distribution of 0.2 (e.g., 20% likelihood of occurrence) for the medical imaging data 112 to have no motion, a probability distribution of 0.6 (e.g., 60% likelihood of occurrence) for the medical imaging data 112 to have mild motion, a probability distribution of 0.1 (e.g., 10% likelihood of occurrence) for the medical imaging data 112 to have moderate motion, and a probability distribution of 0.1 (e.g., 10% likelihood of occurrence) for the medical imaging data 112 to have severe motion. Therefore, in the non-limiting example shown in FIG. 5, the medical imaging data 112 can be labeled with the second classification 504 that corresponds to mild motion.

FIG. 6 illustrates an example, non-limiting system 600 in accordance with one or more embodiments described herein. Repetitive description of like elements employed in other embodiments described herein is omitted for sake of brevity. The system 600 includes the probability distribution of degree of motion 404 and the motion score 406. In the embodiment shown in FIG. 6, the probability distribution of degree of motion 404 includes the grading scale with the first classification 502, the second classification 504, the third classification 506 and the fourth classification 508. Furthermore, in the embodiment shown in FIG. 6, the motion score 406 includes a motion score value 602. A value of the motion score value 602 can be within a motion score value range. For example, in an embodiment, the motion score value range can be from 0.0 to 1.0. As such, in an embodiment, a value of the motion score 406 can greater than or equal to 0.0, and less than or equal to 1.0. In the non-limiting example shown in FIG. 6, a value of the motion score value 602 can be 0.3. Furthermore, the value of 0.3 can correspond to the second classification 504 associated with mild motion in the medical imaging data 112. For instance, a motion score value of 0.0 can correspond to no motion in the medical imaging data 112 (e.g., a motion score value of 0.0 can correspond to the first classification 502), a motion score value of 0.3 can correspond to mild motion in the medical imaging data 112 (e.g., a motion score value of 0.3 can correspond to the second classification 504), a motion score value of 0.6 can correspond to moderate motion in the medical imaging data 112 (e.g., a motion score value of 0.6 can correspond to the third classification 506), and a motion score value of 1.0 can correspond to severe motion in the medical imaging data 112 (e.g., a motion score value of 1.0 can correspond to the fourth classification 508). Accordingly, the motion score 406 can be a normalized motion score of the probability distribution of degree of motion 404.

Figure 7:
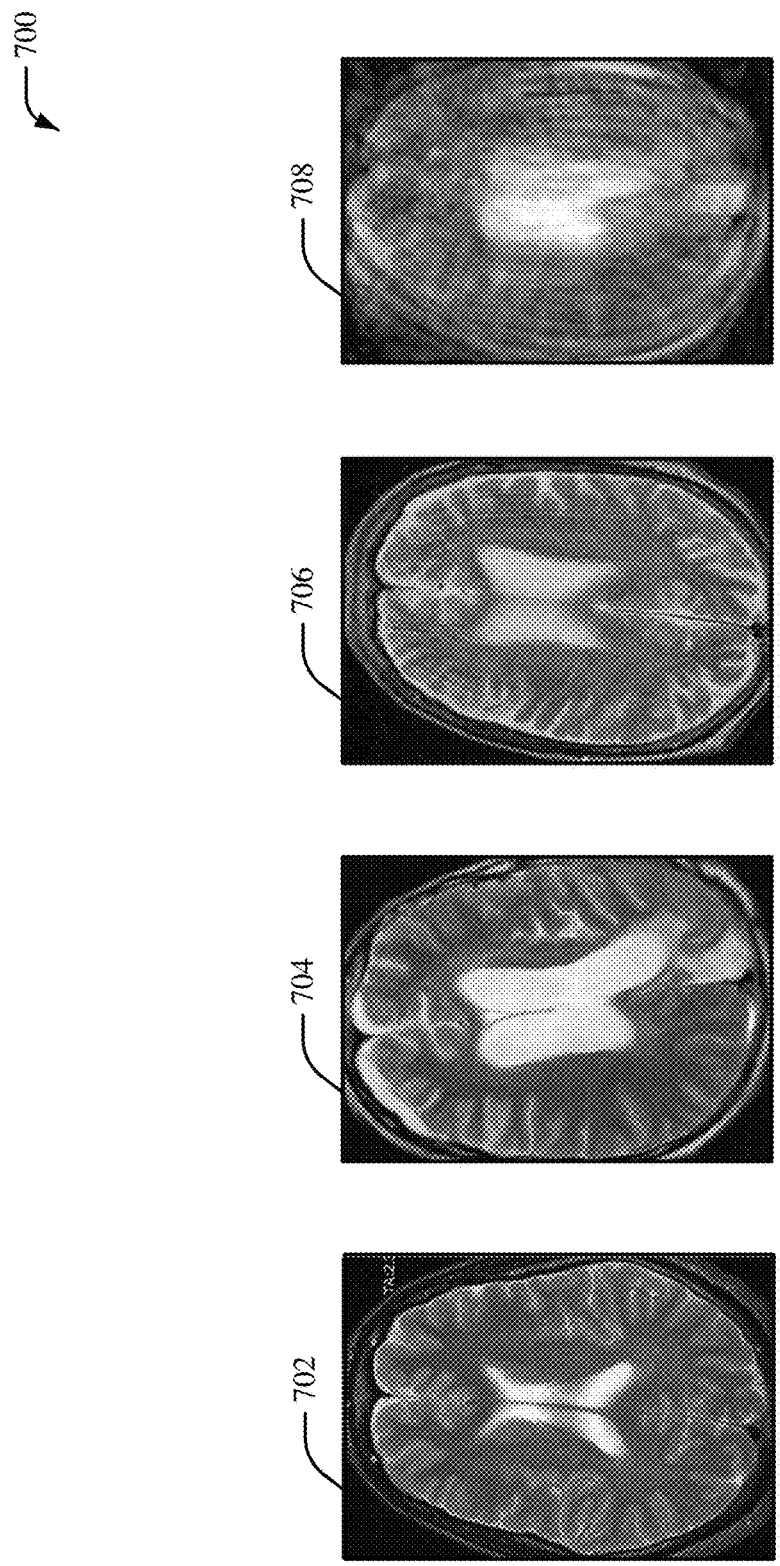
FIG. 7 illustrates example medical imaging data, in accordance with one or more embodiments described herein.

FIG. 7 illustrates an example, non-limiting system 700 in accordance with one or more embodiments described herein. Repetitive description of like elements employed in other embodiments described herein is omitted for sake of brevity. The system 700 includes medical imaging data 702, medical imaging data 704, medical imaging data 706 and medical imaging data 708. The medical imaging data 702, the medical imaging data 704, the medical imaging data 706 and/or the medical imaging data 708 can correspond to the medical imaging data 112 provided to the image quality component 102. Furthermore, the medical imaging data 702, the medical imaging data 704, the medical imaging data 706 and/or the medical imaging data 708 can be generated by a medical imaging device (e.g., the medical imaging device 304) during a scan performed via the medical imaging device (e.g., the medical imaging device 304). In an example, the medical imaging data 702, the medical imaging data 704, the medical imaging data 706 and/or the medical imaging data 708 can be an MRI image of an anatomical region of a patient such as, for example, a brain. In an embodiment, the image quality component 102 (e.g., the machine learning component 104 and/or the scoring component 106) can analyze the medical imaging data 702, the medical imaging data 704, the medical imaging data 706 and/or the medical imaging data 708 to determine a degree of motion in the medical imaging data 702, the medical imaging data 704, the medical imaging data 706 and/or the medical imaging data 708. In an example, the image quality component 102 (e.g., the machine learning component 104 and/or the scoring component 106) can determine that the medical imaging data 702 includes no motion (e.g., the medical imaging data 702 corresponds to the first classification 502), the medical imaging data 704 includes mild motion (e.g., the medical imaging data 704 corresponds to the second classification 504), the medical imaging data 706 includes moderate motion (e.g., the medical imaging data 706 corresponds to the third classification 506), and the medical imaging data 708 includes severe motion (e.g., the medical imaging data 708 corresponds to the fourth classification 508). In certain embodiments, the image quality component 102 (e.g., the machine learning component 104 and/or the scoring component 106) can initiate a rescan by a medical imaging device (e.g., by the medical imaging device 304) in response to the medical imaging data 708.

Figure 8:
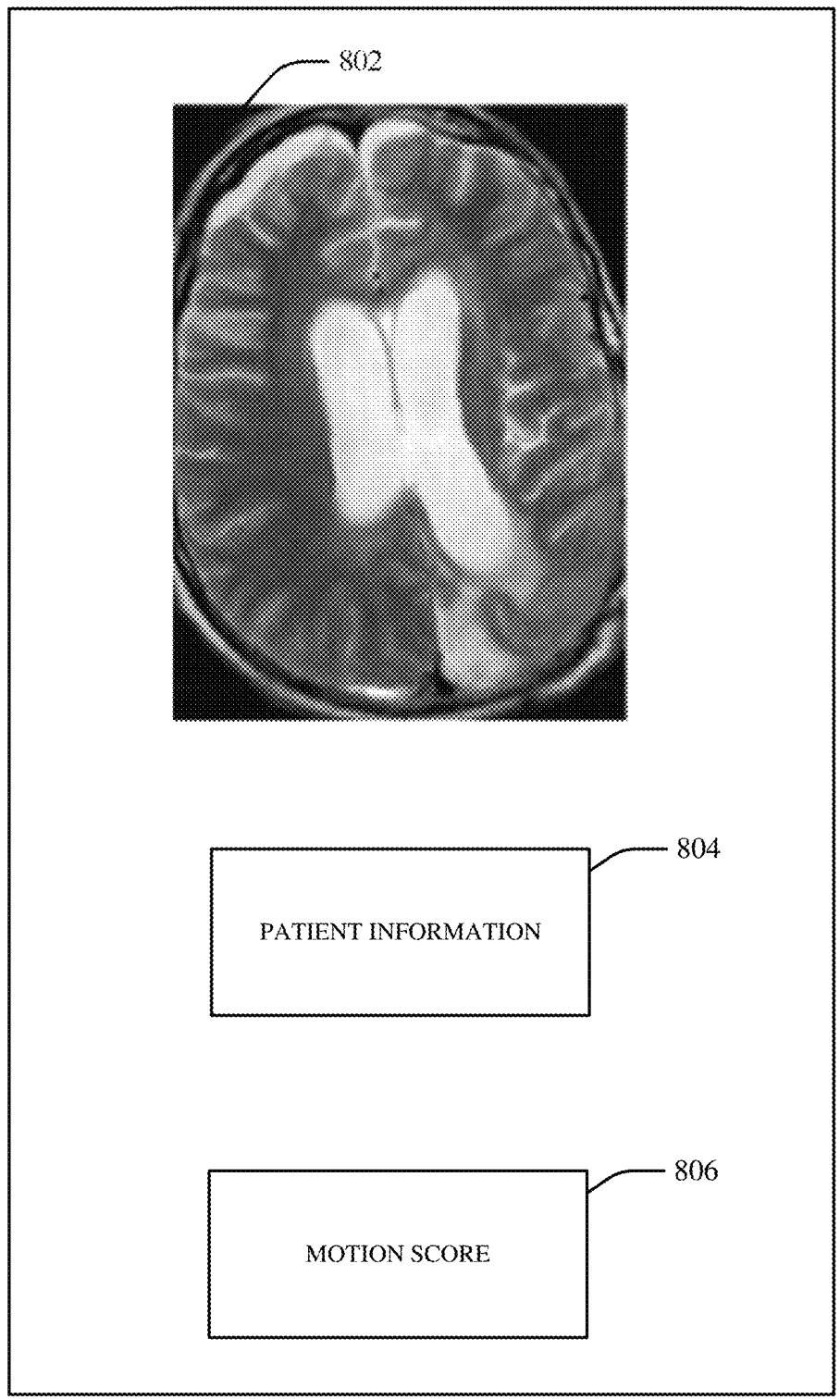
FIG. 8 illustrates an example user interface, in accordance with one or more embodiments described herein.

FIG. 8 illustrates an example user interface 800, in accordance with various aspects and implementations described herein. Repetitive description of like elements employed in other embodiments described herein is omitted for sake of brevity. The user interface 800 can be a display environment for medical imaging data and/or motion score data associated with medical imaging data. Furthermore, in an embodiment, the user interface 800 can be a graphical user interface presented on a display. In certain embodiments, the user interface 800 can be displayed via a user device (e.g., the user device 306). The user interface 800 can include medical imaging data 802. In one embodiment, the medical imaging data 802 can be medical imaging data generated by a medical imaging device (e.g., the medical imaging device 304). For example, the medical imaging data 802 can be displayed as a medical image associated with an anatomical region (e.g., a brain, etc.) of a patient. In an embodiment, the medical imaging data 802 can correspond to the medical imaging data 112 received by the image quality component 102. The user interface 800 can also include patient information 804, in certain embodiments. The patient information 804 can include information regarding a patient (e.g., a patient body) associated with the medical imaging data 802. For example, the patient information 804 can include patient identification data, patient medical record data, patient medical chart data, patient medical history data, patient medical monitoring data, and/or other patient data. The user interface 800 can additionally or alternatively include a motion score 806. The motion score 806 can be a motion score for the medical imaging data 802. For example, the motion score 806 can indicate a degree of motion in the medical imaging data 802. In certain embodiments, the motion score 806 can indicate whether the medical imaging data 802 includes no motion, mild motion, moderate motion, or severe motion. In certain embodiments, the motion score 806 can be associated with an alert that provides a visual notification and/or an audio notification in response to a determination that the motion score 806 satisfies a defined criterion. In certain embodiments, the motion score 806 can be determined by the image quality component 102 (e.g., the machine learning component 104, the scoring component 106 and/or the alert component 202). In certain embodiments, information associated with the motion score data 114 and/or the motion score 406 can be presented via the motion score 806.

Figure 9:
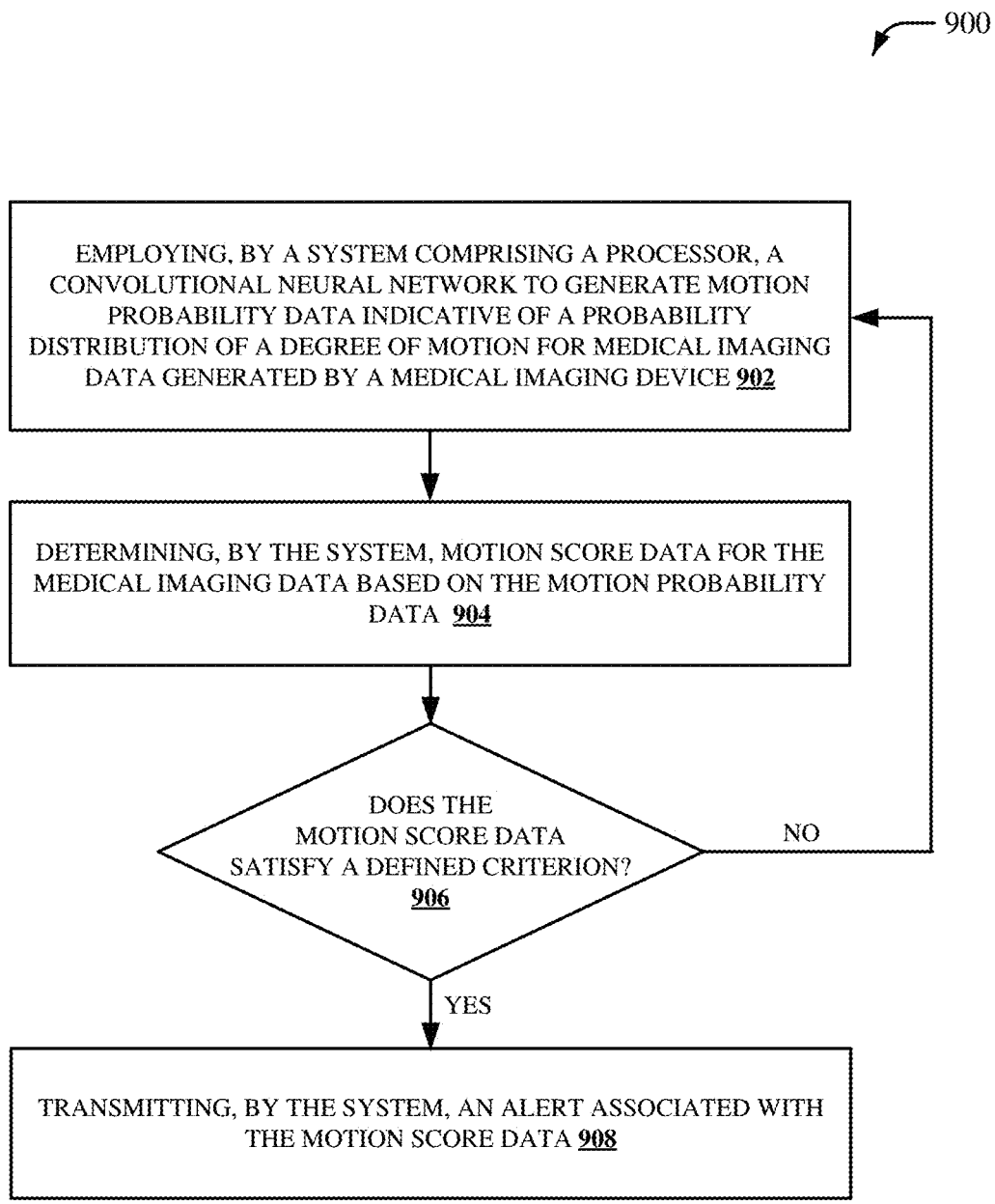
FIG. 9 depicts a flow diagram of an example method for facilitating determining degree of motion using machine learning to improve medical image quality, in accordance with one or more embodiments described herein.

FIG. 9 illustrates a flow diagram of an example, non-limiting computer-implemented method 900 for determining degree of motion using machine learning to improve medical image quality in accordance with one or more embodiments described herein. Repetitive description of like elements employed in other embodiments described herein is omitted for sake of brevity.

At 902, a convolutional neural network is employed, by a system comprising a processor (e.g., by the machine learning component 104), to generate motion probability data indicative of a probability distribution of a degree of motion for medical imaging data generated by a medical imaging device. The medical imaging data can be two-dimensional medical imaging data and/or three-dimensional medical imaging data generated by one or more medical imaging devices. For instance, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an MRI device, an x-ray device, a CT device, another type of medical imaging device, etc. In one example, the medical imaging data can include one or more MRI images. In an aspect, the motion probability data can be indicative of a probability distribution of a degree of motion introduced during a scan performed via a medical imaging device. In an example, the motion probability data can be indicative of a probability distribution of a degree of motion for an MRI image generated during an MRI scan by an MRI device. In another aspect, the convolutional neural network can include a set of convolutional layers associated with upsampling and/or downsampling. Furthermore, in certain embodiments, the convolutional neural network can include a contracting path of convolutional layers and/or an expansive path of convolutional neural layers. In certain embodiments, the convolutional neural network can be an artificial recurrent neural network. In yet certain embodiments, the convolutional neural network can be a CNN LSTM network.

At 904, motion score data for the medical imaging data is determined, by the system (e.g., by the scoring component 106), based on the motion probability data. The motion score data can include a motion score that defines a degree of motion in the medical imaging data. In certain embodiments, the motion score data can be determined based on context data indicative of context with the medical imaging data with respect to a medical condition. Additionally or alternatively, the motion score data can be determined based on context data indicative of context with the medical imaging data 112 with respect to a patient identity. In certain embodiments, a normalized expected value of the probability distribution included in the motion probability data can be calculated to generate the motion score data.

At 906, it is determined (e.g., by the scoring component 106) whether the motion score data satisfies a defined criterion. For example, it can be determined wither the motion score data corresponds to a certain degree of motion. If no, the computer-implemented method 900 returns to 902. If yes, the computer-implemented method 900 proceeds to 908.

At 908, an alert associated with the motion score data is transmitted by the system (e.g., by the alert component 202). For example, the alert can be transmitted via a medical imaging device. In another example, the alert can be transmitted in a human-interpretable format for a graphical user interface of a user device. In certain embodiments, the alert can initiate a rescan of medical imaging data via a medical imaging device to generate new medical imaging data for an anatomical region associated with the medical imaging data.

In certain embodiments, the computer-implemented method 900 can include generating, by the system (e.g., by the machine learning component 104), first motion probability data for a first medical image associated with an anatomical region. Additionally, the computer-implemented method 900 can include generating, by the system (e.g., by the machine learning component 104), second motion probability data for a second medical image associated with the anatomical region. In certain embodiments, the determining the motion score data can include determining the motion score data based on a comparison of the first motion probability data and the second motion probability data.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Moreover, because at least employing a convolutional neural network, etc. is established from a combination of electrical and mechanical components and circuitry, a human is unable to replicate or perform processing performed by the image quality component 102 (e.g., the machine learning component 104, the scoring component 106 and/or the alert component 202) disclosed herein. For example, a human is unable to perform machine learning associated with a convolutional neural network, etc.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 10:
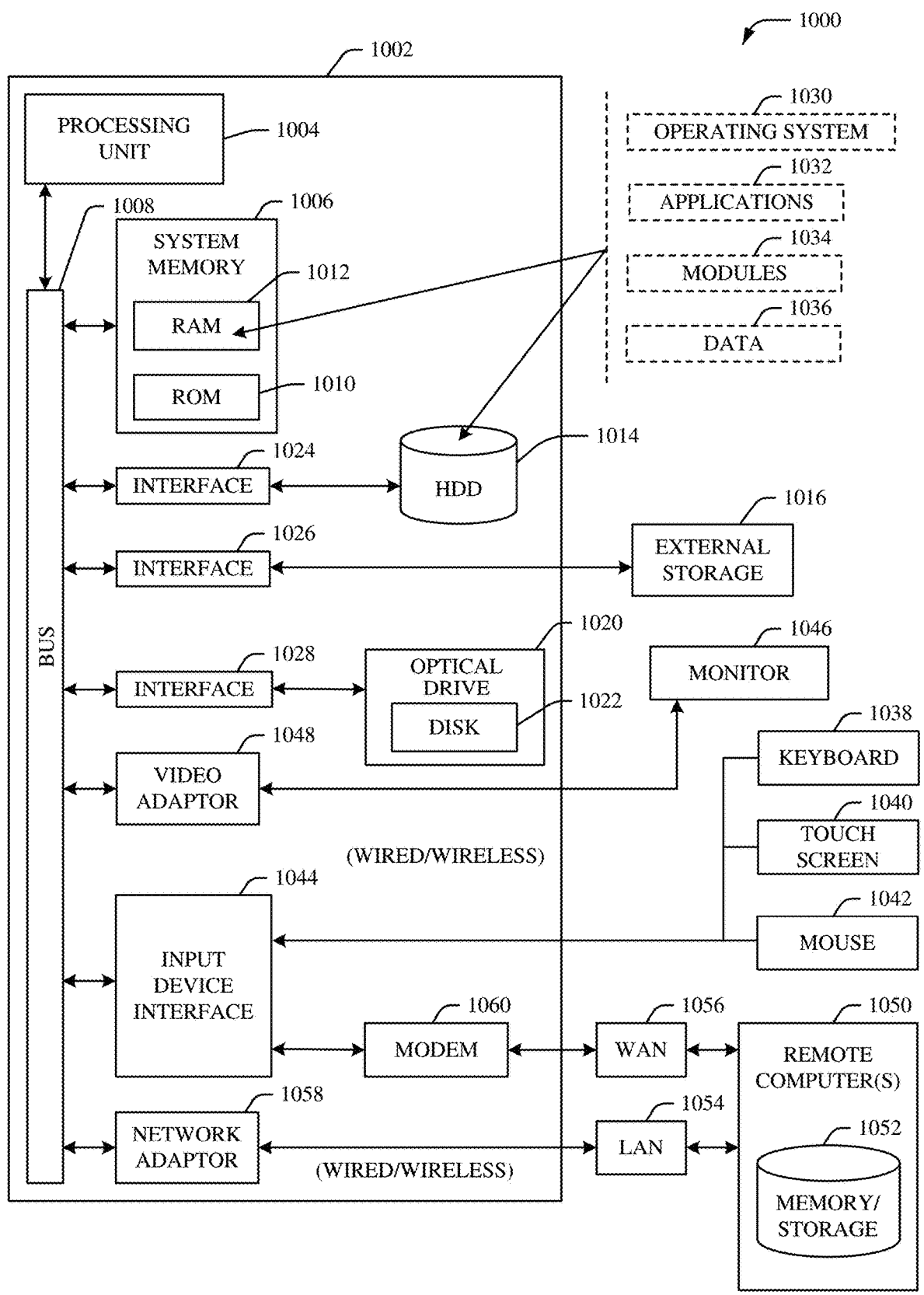
FIG. 10 is a schematic block diagram illustrating a suitable operating environment.

In order to provide additional context for various embodiments described herein, FIG. 10 and the following discussion are intended to provide a brief, general description of a suitable computing environment 1000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 10, the example environment 1000 for implementing various embodiments of the aspects described herein includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures can also be employed as the processing unit 1004.

The system bus 1008 can be any of several types of bus structure that can further interconnect to a memory bus (with or without a memory controller), a peripheral bus, and a local bus using any of a variety of commercially available bus architectures. The system memory 1006 includes ROM 1010 and RAM 1012. A basic input/output system (BIOS) can be stored in a non-volatile memory such as ROM, erasable programmable read only memory (EPROM), EEPROM, which BIOS contains the basic routines that help to transfer information between elements within the computer 1002, such as during startup. The RAM 1012 can also include a high-speed RAM such as static RAM for caching data.

The computer 1002 further includes an internal hard disk drive (HDD) 1014 (e.g., EIDE, SATA), one or more external storage devices 1016 (e.g., a magnetic floppy disk drive (FDD) 1016, a memory stick or flash drive reader, a memory card reader, etc.) and an optical disk drive 1020 (e.g., which can read or write from a CD-ROM disc, a DVD, a BD, etc.). While the internal HDD 1014 is illustrated as located within the computer 1002, the internal HDD 1014 can also be configured for external use in a suitable chassis (not shown). Additionally, while not shown in environment 1000, a solid state drive (SSD) could be used in addition to, or in place of, an HDD 1014. The HDD 1014, external storage device(s) 1016 and optical disk drive 1020 can be connected to the system bus 1008 by an HDD interface 1024, an external storage interface 1026 and an optical drive interface 1028, respectively. The interface 1024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. The systems and methods described herein can be implemented utilizing various commercially available operating systems or combinations of operating systems.

Computer 1002 can optionally comprise emulation technologies. For example, a hypervisor (not shown) or other intermediary can emulate a hardware environment for operating system 1030, and the emulated hardware can optionally be different from the hardware illustrated in FIG. 10. In such an embodiment, operating system 1030 can comprise one virtual machine (VM) of multiple VMs hosted at computer 1002. Furthermore, operating system 1030 can provide runtime environments, such as the Java runtime environment or the .NET framework, for applications 1032. Runtime environments are consistent execution environments that allow applications 1032 to run on any operating system that includes the runtime environment. Similarly, operating system 1030 can support containers, and applications 1032 can be in the form of containers, which are lightweight, standalone, executable packages of software that include, e.g., code, runtime, system tools, system libraries and settings for an application.

Further, computer 1002 can be enable with a security module, such as a trusted processing module (TPM). For instance with a TPM, boot components hash next in time boot components, and wait for a match of results to secured values, before loading a next boot component. This process can take place at any layer in the code execution stack of computer 1002, e.g., applied at the application execution level or at the operating system (OS) kernel level, thereby enabling security at any level of code execution.

A user can enter commands and information into the computer 1002 through one or more wired/wireless input devices, e.g., a keyboard 1038, a touch screen 1040, and a pointing device, such as a mouse 1042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1004 through an input device interface 1044 that can be coupled to the system bus 1008, but can be connected by other interfaces, such as a parallel port, an IEEE 1394 serial port, a game port, a USB port, an IR interface, a BLUETOOTH® interface, etc.

A monitor 1046 or other type of display device can be also connected to the system bus 1008 via an interface, such as a video adapter 1048. In addition to the monitor 1046, a computer typically includes other peripheral output devices (not shown), such as speakers, printers, etc.

The computer 1002 can operate in a networked environment using logical connections via wired and/or wireless communications to one or more remote computers, such as a remote computer(s) 1050. The remote computer(s) 1050 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1052 is illustrated. The logical connections depicted include wired/wireless connectivity to a local area network (LAN) 1054 and/or larger networks, e.g., a wide area network (WAN) 1056. Such LAN and WAN networking environments are commonplace in offices and companies, and facilitate enterprise-wide computer networks, such as intranets, all of which can connect to a global communications network, e.g., the Internet.

When used in a LAN networking environment, the computer 1002 can be connected to the local network 1054 through a wired and/or wireless communication network interface or adapter 1058. The adapter 1058 can facilitate wired or wireless communication to the LAN 1054, which can also include a wireless access point (AP) disposed thereon for communicating with the adapter 1058 in a wireless mode.

When used in a WAN networking environment, the computer 1002 can include a modem 1060 or can be connected to a communications server on the WAN 1056 via other means for establishing communications over the WAN 1056, such as by way of the Internet. The modem 1060, which can be internal or external and a wired or wireless device, can be connected to the system bus 1008 via the input device interface 1044. In a networked environment, program modules depicted relative to the computer 1002 or portions thereof, can be stored in the remote memory/storage device 1052. It will be appreciated that the network connections shown are example and other means of establishing a communications link between the computers can be used.

When used in either a LAN or WAN networking environment, the computer 1002 can access cloud storage systems or other network-based storage systems in addition to, or in place of, external storage devices 1016 as described above. Generally, a connection between the computer 1002 and a cloud storage system can be established over a LAN 1054 or WAN 1056 e.g., by the adapter 1058 or modem 1060, respectively. Upon connecting the computer 1002 to an associated cloud storage system, the external storage interface 1026 can, with the aid of the adapter 1058 and/or modem 1060, manage storage provided by the cloud storage system as it would other types of external storage. For instance, the external storage interface 1026 can be configured to provide access to cloud storage sources as if those sources were physically connected to the computer 1002.

The computer 1002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 11:
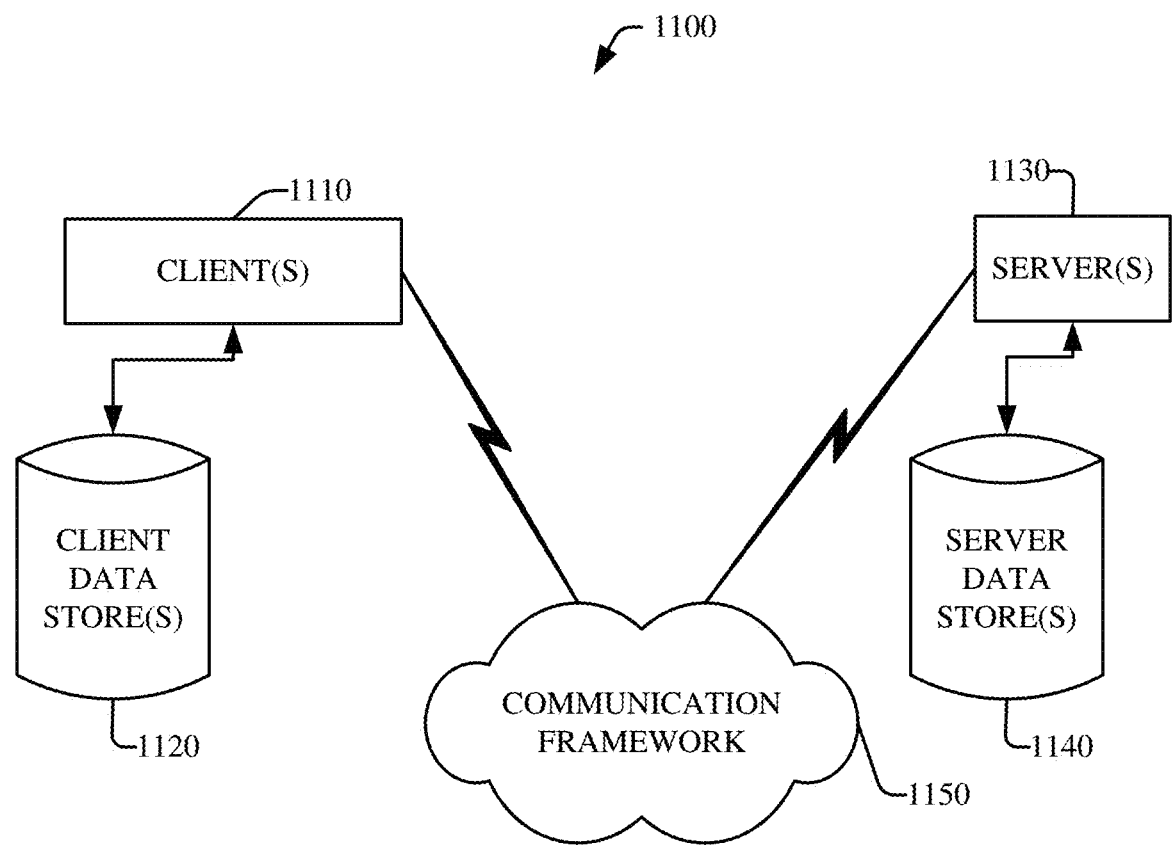
FIG. 11 is a schematic block diagram of a sample-computing environment.

FIG. 11 is a schematic block diagram of a sample-computing environment 1100 with which the subject matter of this disclosure can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing this disclosure, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. The client(s) 1110 are operatively connected to one or more client data store(s) 1120 that can be employed to store information local to the client(s) 1110. Similarly, the server(s) 1130 are operatively connected to one or more server data store(s) 1140 that can be employed to store information local to the servers 1130.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
 a memory that stores computer executable components; and
 a processor that executes computer executable components stored in the memory, wherein the computer executable components comprise:
  a machine learning component that generates, based on a convolutional neural network, motion probability data indicative of a probability distribution of a degree of motion for medical imaging data generated by a medical imaging device; and
  a scoring component that determines motion score data for the medical imaging data based on the motion probability data and context data indicative of a context associated with the medical imaging data with respect to a medical condition and a patient identity, wherein the context indicates a degree of criticality of accuracy of a scan of an anatomical region associated with the patient identity by the medical imaging device, and wherein the degree of criticality of the accuracy of the scan is determined based on whether the medical condition is determined to be a life threatening medical condition associated with the patient identity.

2. The system of claim 1, wherein the machine learning component generates the motion probability data based on an artificial recurrent neural network.

3. The system of claim 1, wherein the scoring component calculates a normalized expected value of the probability distribution to generate the motion score data.

4. The system of claim 1, wherein the machine learning component generates first motion probability data for a first medical image associated with the anatomical region and second motion probability data for a second medical image associated with the anatomical region.

5. The system of claim 4, wherein the scoring component determines the motion score data based on a comparison of the first motion probability data and the second motion probability data.

6. The system of claim 4, wherein the first medical image is associated with a first scan technique with respect to the anatomical region and the second medical image is associated with a second scan technique with respect to the anatomical region.

7. The system of claim 4, wherein the first medical image is associated with a first contrast level and the second medical image is associated with a second contrast level.

8. The system of claim 1, wherein the scoring component modifies initial motion score data to generate the motion score data based on the context data indicative of the context that indicates the degree of criticality of the accuracy of the scan of the anatomical region associated with the patient identity and based on a weight value associated with the degree of criticality, wherein the context relates to a scan type of the scan, a medical purpose of the scan, and a medical history associated with the patient identity, wherein, based on the context, the degree of criticality of the accuracy of the scan is determined from a group of degrees of criticality comprising a lower degree of criticality of the accuracy of the scan and a higher degree of criticality of the accuracy of the scan, wherein the higher degree of criticality is higher than the lower degree of criticality, wherein the higher degree of criticality of the accuracy of the scan is associated with the life threatening medical condition, and wherein the lower degree of criticality of the accuracy of the scan is associated with a non-life threatening medical condition.

9. The system of claim 1, wherein the computer executable components further comprise:
 an alert component that transmits an alert in response to a determination that the motion score data satisfies a defined criterion that indicates an impermissibly high degree of motion associated with the medical imaging data obtained from the scan; and
 an image quality component that, in response to the alert indicating the impermissibly high degree of motion associated with the medical imaging data obtained from the scan, initiates a rescan of the anatomical region associated with the patient identity by the medical imaging device.

10. A method, comprising:
 employing, by a system comprising a processor, a convolutional neural network to generate motion probability data indicative of a probability distribution of a degree of motion for medical imaging data generated by a medical imaging device; and
 determining, by the system, motion score data for the medical imaging data based on the motion probability data and context data indicative of a context associated with the medical imaging data with respect to a medical condition and a patient identity, wherein the context indicates a level of criticality of accuracy of a scan of an anatomical region associated with the patient identity, and wherein the level of criticality of the accuracy of the scan is determined based on whether the medical condition is deemed to be a life threatening medical condition.

11. The method of claim 10, wherein the employing comprises employing an artificial recurrent neural network to generate the motion probability data.

12. The method of claim 10, further comprising:
 calculating, by the system, a normalized expected value of the probability distribution.

13. The method of claim 10, further comprising:
 generating, by the system, first motion probability data for a first medical image associated with the anatomical region; and
 generating, by the system, second motion probability data for a second medical image associated with the anatomical region.

14. The method of claim 13, wherein the determining of the motion score data comprises determining the motion score data based on a comparison of the first motion probability data and the second motion probability data.

15. The method of claim 10, wherein the determining of the motion score data comprises modifying initial motion score data to determine the motion score data based on the context data indicative of the context that indicates the level of criticality of the accuracy of the scan of the anatomical region associated with the patient identity, wherein the context relates to at least one of a scan type of the scan, a medical purpose of the scan, or a medical history associated with the patient identity, wherein the level of criticality of the accuracy of the scan is identified from a group of levels of criticality comprising a first level of criticality of the accuracy of the scan and a second level of criticality of the accuracy of the scan, wherein the second level of criticality is higher than the first level of criticality, wherein the second level of criticality of the accuracy of the scan is associated with the life threatening medical condition, and wherein the first level of criticality of the accuracy of the scan is associated with a non-life threatening medical condition.

16. The method of claim 10, further comprising:
   transmitting, by the system, an alert in response to a determination that the motion score data satisfies a defined criterion.

17. A non-transitory computer readable storage device comprising instructions that, in response to execution, cause a system comprising a processor to perform operations, comprising:
   generating, using a convolutional neural network, motion probability data indicative of a probability distribution of a degree of motion for medical imaging data generated by a medical imaging device; and
   determining motion score data for the medical imaging data based on the motion probability data and context data relating to a context associated with the medical imaging data with respect to a medical condition and a patient identity, wherein the context indicates a degree of criticality of accuracy of a scan of an anatomical region associated with the patient identity, and wherein the degree of criticality of the accuracy of the scan is determined based on whether the medical condition is considered to be a life threatening medical condition.

18. The non-transitory computer readable storage device of claim 17, wherein the operations further comprise:
   calculating a normalized expected value of the probability distribution.

19. The non-transitory computer readable storage device of claim 17, wherein the operations further comprise:
   generating first motion probability data for a first medical image associated with the anatomical region; and
   generating second motion probability data for a second medical image associated with the anatomical region.

20. The non-transitory computer readable storage device of claim 19, wherein the determining of the motion score data comprises determining the motion score data based on a comparison of the first motion probability data and the second motion probability data.

\* \* \* \* \*